United States Patent [19]
Beck

[11] Patent Number: 4,871,851
[45] Date of Patent: Oct. 3, 1989

[54] CYANO-TRICHLORO-PYRIDO-PYRIMIDINE AND A PROCESS FOR PREPARING CYANO-TRICHLORO-PYRIDO-PYRIMIDINE

[75] Inventor: Gunther Beck, Leverkusen, Fed. Rep. of Germany

[73] Assignee: Bayer Aktiengesellschaft, Leverkusen, Fed. Rep. of Germany

[21] Appl. No.: 132,502

[22] Filed: Dec. 14, 1987

[30] Foreign Application Priority Data

Dec. 19, 1986 [DE] Fed. Rep. of Germany ....... 3643456

[51] Int. Cl.$^4$ ............................................. C07D 471/04
[52] U.S. Cl. ..................................... 544/279; 544/334
[58] Field of Search .......................................... 544/279

[56] References Cited

U.S. PATENT DOCUMENTS 4,294,969 10/1981 Baldwin et al. ...................... 546/286
4,567,004 1/1986 Blank et al. .......................... 562/459

FOREIGN PATENT DOCUMENTS 460710 11/1949 Canada ................................ 546/286

OTHER PUBLICATIONS

March, Advanced Organic Chem. 3rd Edition, pp. 835–836.
Beck, CA 109–211077n, "Preparation of 2,4,7-trichloropyrido [2,3-d]pyrimidine–6–carbonitrile as a dye intermediate".

*Primary Examiner*—Cecilia Shen
*Attorney, Agent, or Firm*—Sprung Horn Kramer & Woods

[57] ABSTRACT

Cyano-trichloro-pyrido-pyrimidine of the formula

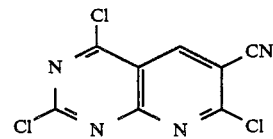

is a new reactive component for dyestuffs containing amino groups. It is obtained by heating the compound of the formula

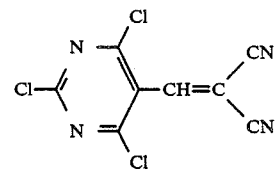

in the presence of Friedel-Crafts catalysts.

8 Claims, No Drawings

CYANO-TRICHLORO-PYRIDO-PYRIMIDINE AND A PROCESS FOR PREPARING CYANO-TRICHLORO-PYRIDO-PYRIMIDINE

The present invention relates to the new compound cyano-trichloro-pyrido-pyrimidine of the formula

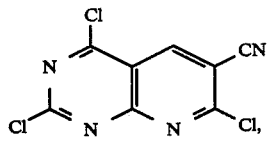

and a process for its preparation.

The process is characterized in that the malodinitrile condensate of the formula

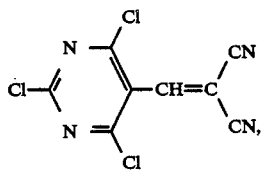

is heated at relatively high temperatures, if appropriate in the presence of Friedel-Crafts compounds.

The reaction is in general carried out in the temperature range from about 100° to 300° C., preferably between 150° and 250° C.

Suitable Friedel-Crafts compounds are described, for example, in "Friedel Crafts and Related Reactions", Volume I, page 201.

Examples which may be mentioned are: AlCl$_3$, AlBr$_3$, BeCl$_2$, CdCl$_2$, ZnCl$_2$, BF$_3$, BCL$_3$, BBr$_3$, GaCl$_3$, TiCl$_4$, TiBr$_4$ ZrCl$_4$, SnCl$_4$, SnBr$_4$, SbCl$_5$, SbCl$_3$, FeCl$_3$ and UCl$_4$.

AlCl$_3$ is particularly preferred.

The Friedel-Crafts compounds are in general employed in an amount of 0.01 to 20% by weight, preferably 0.01 to 10% by weight, based on (II).

The course of the reaction can be represented by the following equation:

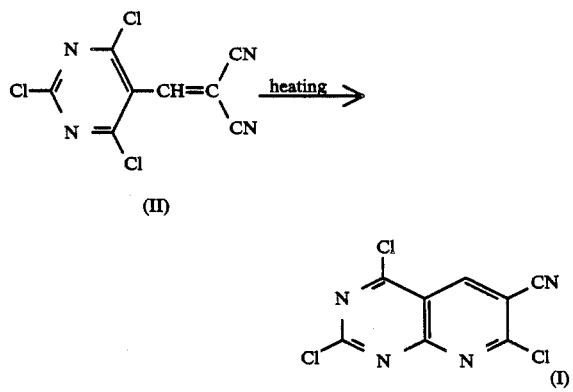

The malodinitrile condensate of the formula (II) used as the starting substance is new and is prepared as follows:

Starting from the known compound 2,4,6-trichloropyrimidine-5-aldehyde (III), which is accessible in a known manner (German Pat. No. A-2,310,334) from barbituric acid, N,N-dimethylformamide and phosphoryl chloride, a so-called Knoevenagel condensation is carried out with malodinitrile (IV) in accordance with the equation

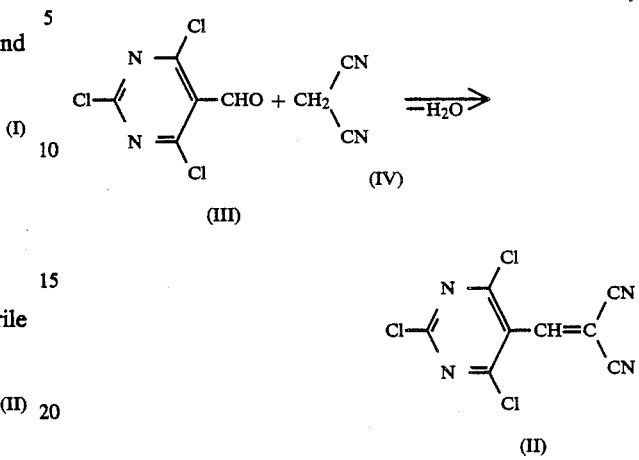

in a manner which is known per se.

Knoevenagel condensations are described, for example, in "Organikum", 13th edition, page 508–510. Further details can be found in the experimental section.

To carry out the process according to the invention, the starting compound of the formula (II) is mixed, if appropriate, with preferably 0.1 to 10% by weight of a Friedel-Crafts compound, preferably aluminium chloride, and heated at the stated temperature range, preferably at 150° to 250° C., until the cyano-trichloropyridopyrimidine of the formula (I) according to the invention has formed. The reaction is advantageously carried out with exclusion of moisture. The time required depends on the one hand on whether the reaction is carried out with or without the addition of Friedel-Crafts catalysts, and on the other hand of course on the nature and amount of the Friedel-Crafts compound and on the reaction temperature. It is in general of the order of 0.1 to 30 hours. Addition of a catalyst reduces the time required.

The reaction can of course also be carried out continuously.

The rearrangement product (I) can be prepared in a pure form by customary methods of organic chemistry, for example by vacuum sublimation. The yields of sublimed, pure white product are between 75 and 95% of theory.

Cyano-trichloro-pyrido-pyrimidine (I) is suitable as a reactive component for the preparation of reactive dyestuffs. For this, for example, it is reacted with equimolar amounts of an azo dyestuff containing amino groups in the customary manner. Reactive dyestuffs which give strong clear dyings with good fastness to washing and light on cotton are thereby obtained.

EXAMPLE 1

30.20 g of malodinitrile condensate (II) were heated at 190° to 195° C. for 5 hours in a glass boat in a drying gun with infinitely adjustable electrical heating and with a rubber bulb ("Orsat" bulb) fixed to its stopcock connector with the stopcock open. Analysis of the cooled reaction product by IR spectroscopy showed that the starting substance was no longer present. Subsequent vacuum sublimation at 180° C./0.1 mb gave a pure white sublimate (I) of melting point 184° C. Sublimatiion residue: 2.09 g. This results in a yield of 93.1% of theory of cyano-trichloropyrido-pyrimidine of the formula (I). I.R. (KBr), $\nu = 3063, 2236, 1595, 1561, 1524, 1421, 1397, 1329, 1228, 1144, 1071, 1064, 948, 863$ and $805 \text{ cm}^{-1}$.

Preparation of the malodinitrile condensate (II)

(a) 1 kg (4.73 mole) of 2,4,6-trichloro-pyrimidine-5-aldehyde (III), 350 g (5.3 mole) of malodinitrile (IV) and 420 g (4.7 mole) of 3-amino-propanoic acid were introduced into six liters of acetonitrile and the reaction mixture was stirred vigorously at room temperature for about 20 hours, with exclusion of moisture. Thereafter, analysis by the layer chromatography showed that the aldehyde (III) was no longer present. The reaction mixture was then stirred into 30 liters of water and the product was subsequently filtered off, washed with water and dried at room temperature. Yield of malodinitrile condensate (II) 933 g (76% of theory). The compound can be recrystallized from toluene or sublimed at, for example, 120° C./0.1 mb. Melting point 160° C. I.R. (KBr): $\nu = 3030, 2240, 1612, 1544, 1492, 1356, 1341, 1302, 1227, 1160, 1145, 911, 890, 829$ and $790 \text{ cm}^{-1}$.

(b) 1.0 g of ammonium acetate and 1.2 g of glacial acetic acid were added to a solution of 21.15 g (0.1 mole) of 2,4,6-trichloro-pyrimidine-5-aldehyde (III) and 13.2 g (0.2 mole of malodinitrile in 100 ml of benzene and the mixture was heated under reflux for 4 hours, using a water separator. Thereafter, the small amount of undissolved material (less than 1 g) was filtered off hot and the filtrate was concentrated in a rotary evaporator. The rotary evaporator residue was subsequently dried on clay and kept in a drying gun at 85° C./0.1 mbar for about 2 hours. 4.85 g of unreacted 2,4,6-trichloro-pyrimidine-5-aldehyde were thereby to be recovered as a sublimate. 15.57 g (60% yield or 77.9% yield, based on the 2,4,6-trichloro-pyrimidine-5-aldehyde reacted) of malodinitrile condensate (II), identical in all its properties with the product obtained under (a), remained as the residue.

EXAMPLE 2

0.2 g of AlCl$_3$ was added to 12.78 g of malodinitrile condensate (II) in an apparatus analogous to that in Example 1 and the mixture was heated at 160° to 165° C. for 1 hour. Analysis of the cooled reaction product by IR spectroscopy showed that the starting substance was no longer present and that the pyrido-pyrimidine (I) had formed.

EXAMPLE 3

0.3 g of AlCl$_3$ was added to 18.60 g of malodinitrile condensate (II) in an apparatus analogous to that in Example 1 and the mixture was heated at about 195° C. for 70 minutes. It was then sublimed at 180° C./0.1 mbar. The pure white sublimate was identical to the sublimation residue of Example 1: 4.63 g, corresponding to a yield of cyano-trichloro-pyrido-pyrimidine (I) of 75%.

EXAMPLE 4

0.029 mole of the dyestuff of the formula

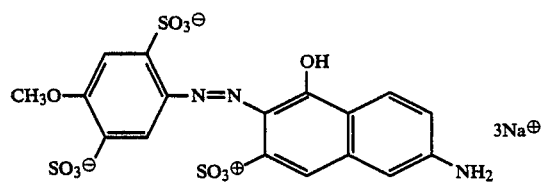

is stirred into 250 ml of water. 7.5 g (0.029 mole) of finely powdered pyrido-pyrimidine of the formula

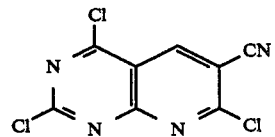

are sprinkled in, the mixture is heated to 40° C. and the hydrochloric acid liberated is neutralized by dropwise addition of dilute sodium carbonate solution.

When the acylation has ended, the condensation product obtained is filtered off with suction, dried and ground. An orange-coloured water-soluble dyestuff powder is obtained. The dyestuff probably corresponds to the formula

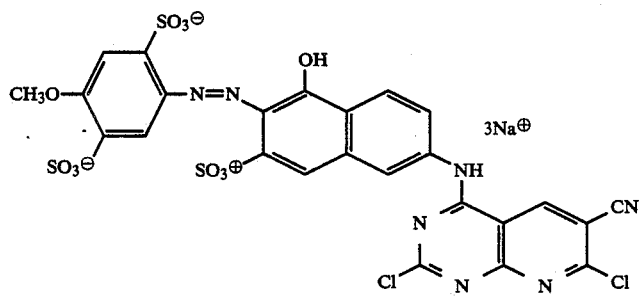

EXAMPLE 5

0.029 mole of the dyestuff of the formula

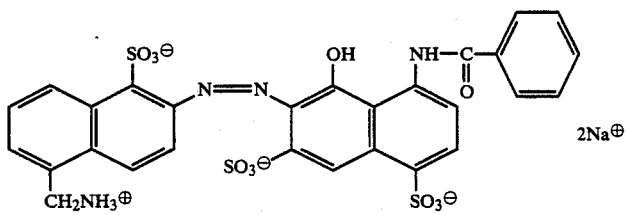

is stirred into 400 ml of water. 7.5 g (0.029 mole) of finely powdered pyrido-pyrimidine of the formula

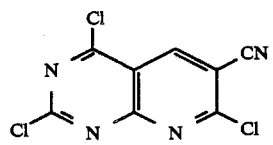

are sprinkled in at room temperature and the pH is kept between 8.5 and 8.8 by dropwise addition of 6% strength lithiumhydroxide solution. When the acylation has ended, the dyestuff is salted out by addition of 200 ml of saturated sodium chloride solution. After filtration with suction, drying and grinding, a red dyestuff powder which readily dissolves in water is obtained. The dyestuff probably corresponds to the formula

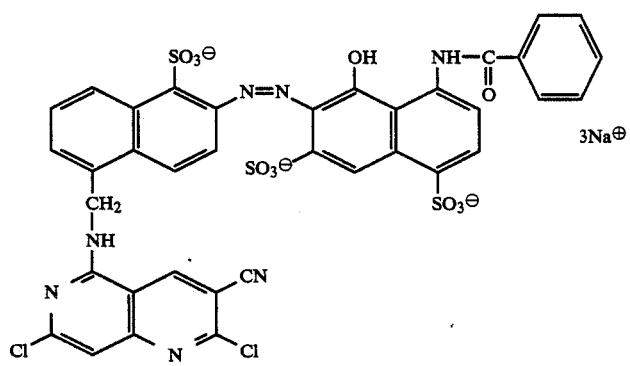

Dyeing instructions 2 parts of the dyestuff obtainable according to Example 5 are dissolved in 100 parts of water.

The solution is added to 1,900 parts of cold water, 60 parts of sodium chloride are added and 100 parts of a cotton hank are introduced into this dyebath.

The temperature is increased to 70° to 80° C., 40 parts of calcined sodium carbonate and a further 60 parts of sodium chloride being added after 30 minutes. The temperature is kept at 70° to 80° C. for 30 minutes, the goods are rinsed and the dyeing is then soaked for 15 minutes in a 0.3% strength boiling solution of an ion-free detergent, rinsed and dried.

A strong bluish-tinged red dyeing with a good fastness to washing and light is obtained.

If 2 parts of the dyestuff obtainable according to Example 4 are used, a clear reddish-tinged orange results on cotton.

I claim:

1. A cyano-trichloro-pyrido-pyrimidine of the formula

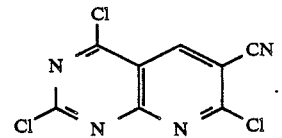

2. A process for the preparation of a cyano-trichloro-pyrido-pyrimidine of the formula comprising heating a malodinitrile condensate of the formula

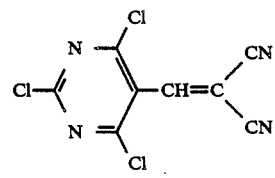

at a temperature of 100° to 300° C., with or without a catalyst, the process being carried out with the exclusion of moisture.

3. A process according to claim 2, wherein it is carried out at a temperature of 150°–250° C.

4. A process according to claim 2, wherein the process is carried out in the presence of Friedel-Crafts catalysts.

5. A process according to claim 4 wherein the Friedel-Crafts catalysts are selected from the group consisting of $AlCl_3$, $AlBr_3$, $BeCl_2$, $CdCl_2$, $ZnCl_2$, $BF_3$, $BCl_3$ $BBr_3$, $GaCl_3$, $TiCl_4$, $TiBr_4$, $ZrCl_4$, $SnCl_4$, $SnBr_4$, $SbCl_5$, $SbCl_3$ $FeCl_3$ and $UCl_4$.

6. A process according to claim 5, wherein the Friedel-Crafts catalyst is AlCl$_3$.

7. A process according to claim 4, wherein the Friedel-Crafts catalyst is applied in an amount of 0.01 to 20% by weight based on the malodinitrile condensate.

8. A process according to claim 7, wherein the Friedel-Crafts catalyst is applied in an amount of 0.01 to 10% by weight.

* * * * *